United States Patent [19] [11] 3,985,453
Nakano et al. [45] Oct. 12, 1976

[54] LIGHT SCATTERING TYPE SMOKE DETECTOR

[75] Inventors: Takeshi Nakano; Kunisige Kurata, both of Owari-Asahi; Yoshihiko Okuda, Izumi; Tsunehiko Araki, Takarazuka, all of Japan

[73] Assignee: Matsushita Electric Works, Ltd., Osaka, Japan

[22] Filed: July 19, 1974

[21] Appl. No.: 489,881

[52] U.S. Cl. ............................. 356/207; 250/574; 340/237 S
[51] Int. Cl.² ........................................ G01N 21/12
[58] Field of Search ............ 356/207, 103; 250/574, 250/239, 237 R; 340/237 S

[56] References Cited
UNITED STATES PATENTS

| | | | |
|---|---|---|---|
| 3,417,392 | 12/1968 | Hansen et al. | 250/574 |
| 3,708,675 | 2/1973 | Tashiro et al. | 356/207 |
| 3,799,670 | 3/1974 | Kohr | 250/239 |
| 3,863,076 | 1/1975 | Steele et al. | 356/207 |
| 3,868,184 | 2/1975 | Marsocci | 356/207 |

Primary Examiner—John K. Corbin
Assistant Examiner—Jon W. Henry
Attorney, Agent, or Firm—Leydig, Voit, Osann, Mayer & Holt

[57] ABSTRACT

A light scattering type smoke detector minimum in size and protected from erroneous operation and from internal accumulation of water drops is provided. The optical system comprises light emitting and receiving elements and light shielding means which are compactly mounted on a base plate at different heights so as normally to prevent light from the emitting element to reach the receiving element. A power source part for the light emitting element disposed at one side of the optical system and an amplifying part for the light receiving element disposed at the other side of the system are housed in an upper lid having drain means, and a lower lid having many small holes for smoke lead-in is attached to the upper lid.

7 Claims, 15 Drawing Figures

LIGHT SCATTERING TYPE SMOKE DETECTOR

This invention relates to light scattering type smoke detectors.

Recent high-rise buildings must be provided with disaster preventing equipment. The smoke detector is one of the most important pieces of disaster preventing equipment.

Generally there have been suggested three kinds of smoke detectors, the first of which is ionization type, the second is smoke permeation type and the third is light scattering type.

The ionization type smoke detector can detect invisibly fine particles and has a high sensitivity but may respond to other than smoke.

The smoke permeation type smoke detector acts on visible smoke but may be accidently triggered when the apparatus is dusted, has a low S/N ratio, is large in size. While this type of detector may be used, for example, in tunnels it is limited in other uses.

While the light scattering type smoke detector is low in sensitivity to black smoke, it is high in sensitivity to white smoke, which makes it possible to obtain a high S/N ratio.

The light scattering type smoke detector has the favorable features described above but is required on the other hand to contain a light emitting element, a light receiving element, an oscillator for the light emitting element and an amplifier for the light receiving element, all of which tend to make the unit large in size. In the present invention, the problem of the light scattering type smoke detector tending to become large has been solved by arranging an optical system along a diametrical line of the unit with an oscillator unit on one side and amplifier unit the other side of said optical system, and arranging the light shielding means or barrier member forming the optical system in a depending orientation.

A main object of the present invention is to provide a smoke detector which can be made small.

Another object of the present invention is to provide a smoke detector which can prevent a misoperation by preventing light emitted from the light emitting element and reflected by any object other than smoke to be detected from entering the light receiving element.

A further object of the present invention is to provide a smoke detector which can prevent a misoperation by any disturbing waves.

A further object of the present invention is to provide a smoke detector wherein water drops deposited on the upper surface of the body can be made to flow out of the device through cut parts, without accumulating within.

An embodiment of the present invention shall be explained in the following with reference to the accompanying drawings, in which.

Figure 1:
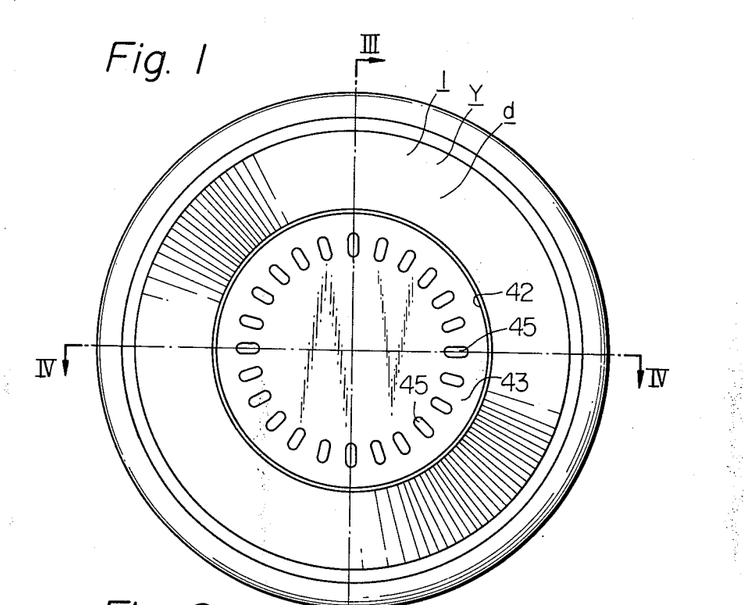
FIG. 1 is an elevation of a smoke detector of the present invention.
Figure 2:
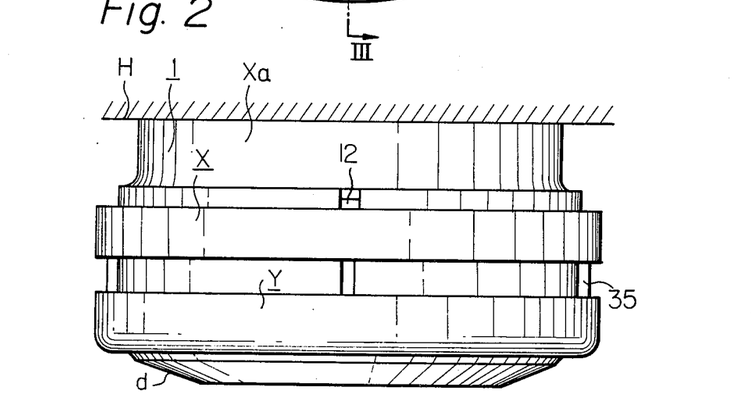
FIG. 2 is a side view of the same.
Figure 3:
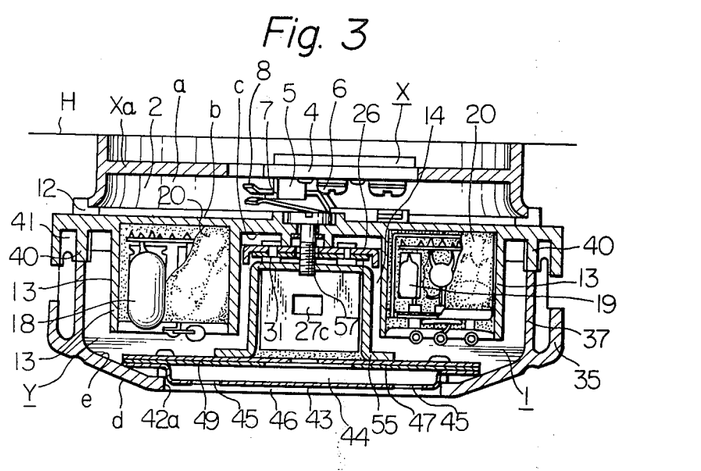
FIG. 3 is a sectioned view on line III—III in FIG. 1.

In FIGS. 1 and 2, item 1 is a circular detector body comprising an upper lid X and lower lid Y respectively formed of a synthetic resin so as to be circular. The upper lid X is removably fitted to a base plate Xa which in turn is fitted to a ceiling surface H.

In FIGS. 3, 4, 7 and 9, item 2 is a circular recessed part formed on the lower surface $a$ of the base plate Xa and provided with fitting holes 3 to fit the base plate Xa to the ceiling surface H and with a port 4 for pulling in electric wires. Item 5 is a terminal plate fitted to the recessed part 2. The relative positions of the fitting holes 3 and pulling-in port 4 are such that the pulling-in port 4 is positioned in the center, the terminal plates 5 are positioned parallel to one another and on both sides of this port 4 and the fitting holes 3 are positioned outside the terminal plates 5. Item 6 are screws for fastening electric wires. Each terminal plate 5 is provided with two screws 6, one being for the input wire and the other being for the output wire. Item 7 is an inserting metal blade which is formed at one end of each terminal plate 5 such that it can be disengageably inserted into a receiving blade 8 fitted to the upper surface $b$ of the upper lid X, (see FIG. 9). The receiving blade 8 is formed to be of two blades 8a and 8b so as to hold the inserting blade 7 between them. The upper blade 8a to receive a load is made of a thick plate. The lower blade 8b is made of a thinner resilient plate so as to impart a contact pressure and is fixed to a projecting part 9 so as to rise above the upper surface $b$ of the upper lid X. Item 10 is a mounting screw for each receiving blade 8 and is screwed to the blade 8 through the lower surface of the upper lid X. A circular receiving step 11 to determine the rotary position of the base plate Xa is formed on the upper surface $b$ of the upper lid X. Further, cuts 12 for draining water are properly made in this receiving step 11 so that water drops accumulating on the upper surface $b$ of the upper lid X will flow out through these cuts 12.

Figure 5:
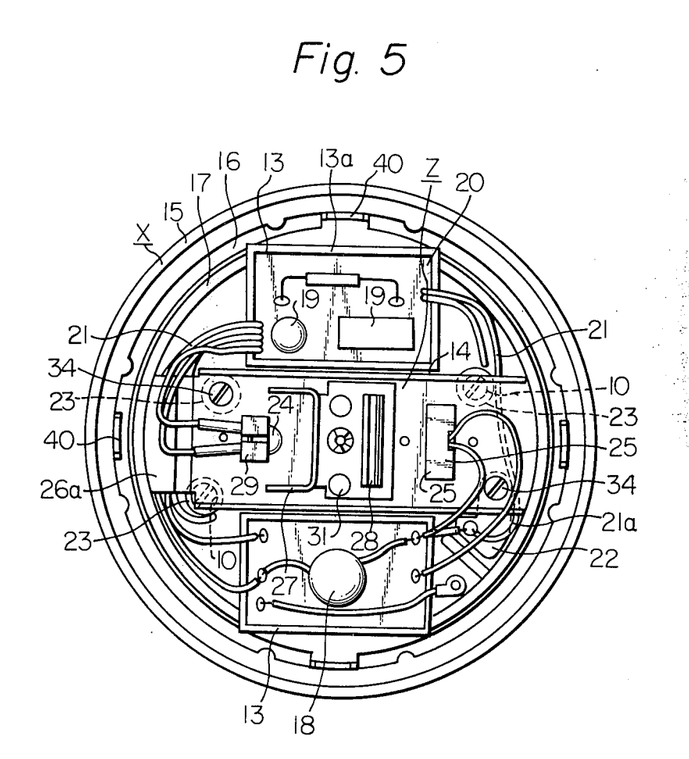
FIG. 5 is a plan view of the detector in FIG. 1, which is shown with a lower lid removed.

In FIG. 5 items 13 are chambers each having a four-sided enclosing wall 13a formed to integrally project from lower surface $c$ of the upper lid X. The chambers 13 are open at their lower surfaces 13b. These right and left chambers 13 have a space 14 provided intermediately between them and are connected with each other through depending peripheral walls 17 formed concentrically with the outer peripheral wall 15 of the upper lid X with a space 16 therebetween. One of the chambers 13 contains a component part 18 forming a current source part and oscillator. The other chamber 13 contains component parts 19 forming an amplifier and a switch part. Silicone rubber 20 is made to flow into the space between the respective component parts to seal them. The respective component parts 18 and 19 are connected through lead wires 21. Two lead wires 21 are connected with the receiving blades 8 on the upper surface $b$ through the upper lid X. Further, among the lead wires 21, a return wire 21a which may be called also a ground wire for preventing electric noise has interposed relay contact 22.

Figure 7:
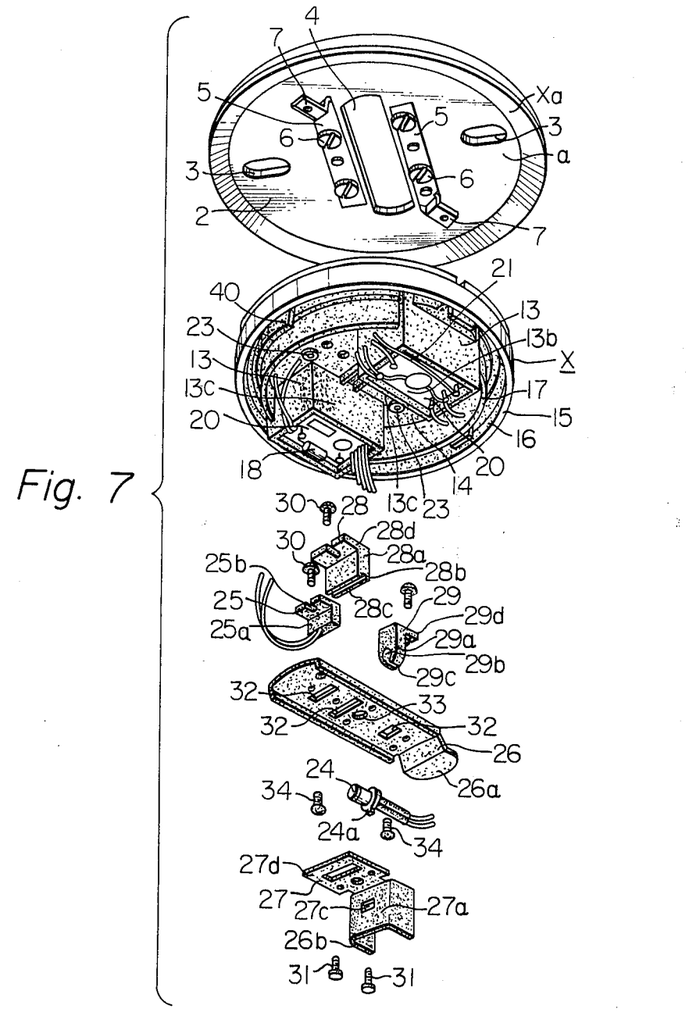
FIG. 7 is a perspective view of an upper lid of FIG. 1 with all assembly parts as disassembled.
Figure 11:
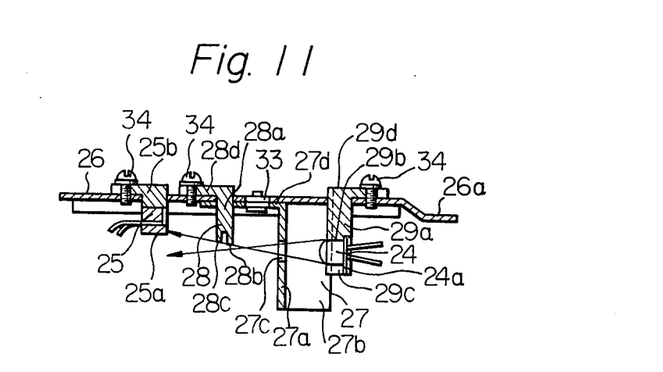
FIG. 11 is a sectioned view of the same.

This contact 22 is received by a small projecting pillar 23 positioned in the space 14 between the respective right and left chambers 13. These small projecting pillars 23 are located in the four corners of the space 14. The screws 10 for the receiving blades 8 are inserted and positioned in the small projections 23 on a diagonal crossing this relay contact 22 and another small projecting pillar 23 so that the head parts of the screws 10 will be hid. Item 24 is a light source connected with the chamber 13 which houses the current source part through the lead wires 21 and using, for example, a light emitting diode for which GaAs is used. Item 25 is a light receiving element (such as, for example, a solar battery) connected with the other chamber 13, which houses the amplifying part and switch part through the lead wires 21. The relationship between the light source 24 and the light receiving element 25 is such that, when light from the light source 24 is projected on the light receiving element 25, the output of said light receiving element 25 will be transmitted to a receiver (not illustrated) by the actions of the amplifier and switch part of the other chamber 13. The above mentioned light source 24 and light receiving element 25 are arranged facing one another on a base plate 26. This base plate 26 is made of a material more thermally durable than the unit body 1 made of a synthetic resin. A metal is used for its material in the illustrated embodiment, but also a thermosetting synthetic resin may be of course utilized. Items 27 and 28 are light shielding plates or barriers positioned between the light source 24 and the light receiving element 25 so that no light will be projected directly on the light receiving element 25. The relation between them is as follows. As shown in FIGS. 7 and 11, the light source 24 is formed to be cylindrical, which is pressed into a split round hole 29b of a vertical piece 29a of an inverted L-shaped supporting frame 29 made of a synthetic resin. The light source 24 is held by the resiliency of the expansion of the splitting groove 29c. A small projection 24a of the light source 24 fits in the splitting groove 29c to prevent relative movement therebetween. The portion 29d is a horizontal piece of the inverted L-shaped supporting frame 29. The light receiving element 25 is also formed to be of an inverted L-shape so that its vertical piece 25a will face the light source 24. The portion 25b is a horizontal piece of the element 25. Further, one barrier 27 is formed of metal to be of an inverted L-shape with portions 27b bent toward the light source 24 on each side of the vertical piece 27a so as to enclose the light source 24. A hole 27c is made in the vertical piece 27a so that light will be projected only in the required direction. The portion 27d is a horizontal piece. The other barrier 28 is formed of a synthetic resin to be of an inverted L-shape, with the lowermost lowest end of the vertical piece 28a being divided into two blade parts 28b and 28c of different lengths. The longer part 28b is positioned toward the light source 24 with the shorter part 28c being positioned toward the light receiving element 25 so as to be edges respectively to cut the light. The portion 28d is a horizontal piece. The supporting frame 29 for the light source 24, light receiving element 25 and one barrier 28 have respectively the vertical pieces 29a, 25a and 28a passed through the base plate 26 so that the respective horizontal pieces 29d, 25d and 28d will be positioned on the upper surface and are fixed with screws 34. The other barrier 27 has the horizontal piece 27d fitted to the lower surface of the base plate 26 and is fixed with rivets 31. An inserting hole 32 is provided for each of the vertical pieces 29a, 25a and 28a. Hole 33 is a through hole made through the horizontal piece 27d of the barrier 27 and center of the base plate 26. This base plate 26 is positioned on the small projections 23 in the four corners and with two screws 34 securing the base plate 26 such that the relay contact 22 and base plate 26 will be electrically connected with each other. Base plate 26 also serves to prevent some of the lead wires 21 from hanging down. The base plate 26 is bent downward at one end 26a so as to hold many lead wires 21. Further, if the light source 24 is removed from the supporting frame 29, it will be possible to pull out the base plate 26 (needless to say, with the light receiving element 25 and its lead wires connected as they are). As shown by the illuminating range in FIG. 11, light from the light source 24 is not projected directly on the light receiving element 25 due to the barriers 27 and 28, hole 27c and longer and shorter blade parts 28b and 28c. These four components 24, 25, 27 and 28 form an optical system part Z. The base plate 26 is also considered to be a part of the optical system part Z.

Figure 6:
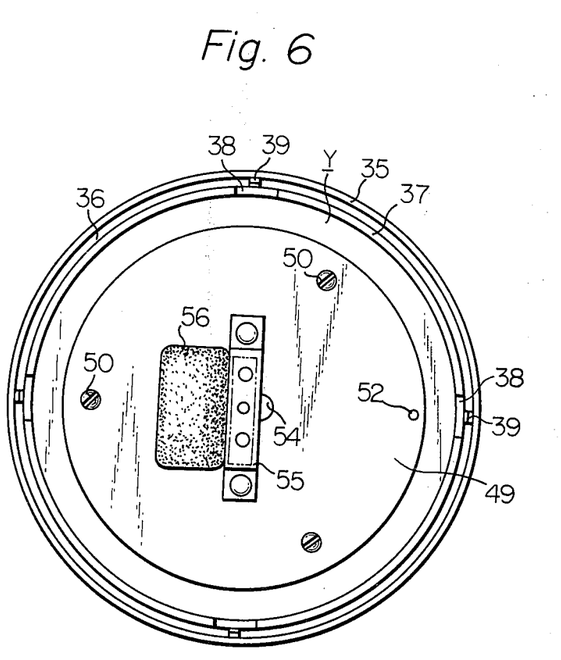
FIG. 6 is another plan view showing the interior of the lower lid shown in FIG. 1.
Figure 8:
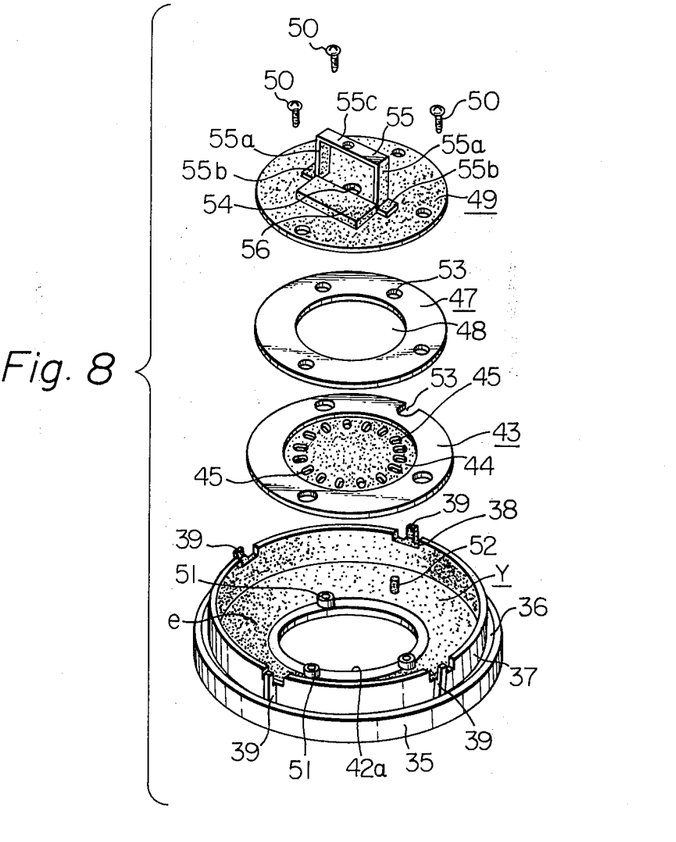
FIG. 8 is a perspective view of the lower lid of FIG. 1 with all parts disassembled.
Figure 9:
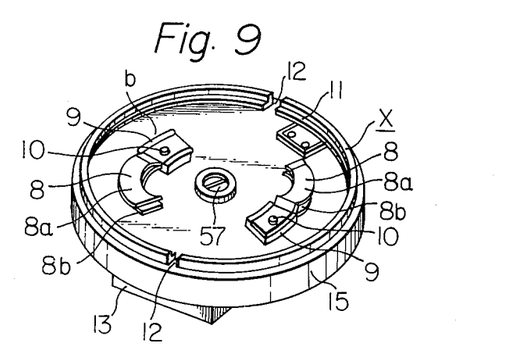
FIG. 9 is a perspective view of a base plate of FIG. 1.
Figure 10:
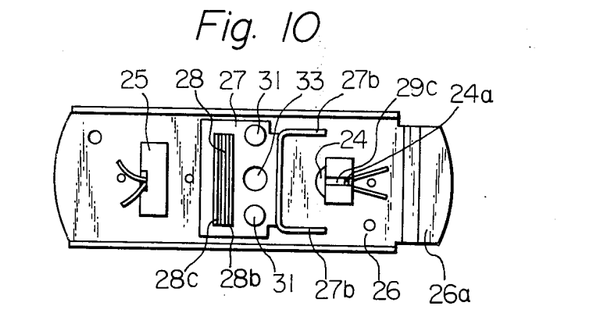
FIG. 10 is a plan view of an optical system in the device of FIG. 1.

Next, the lower lid Y shall be explained. In FIGS. 6 and 8, 35 is an outer peripheral wall of the lower lid Y. An upwardly directed peripheral wall 37 is formed concentrically with the outer peripheral wall 35 with space 36 between them. Items 38 are four notches made in four places at the upper end of the upwardly directed peripheral wall 37. Items 39 are partition pillars in the space 36 positions corresponding to the four notches 38. The upper ends of the partition pillars are substantially flush with the upper end of the upwardly directed peripheral wall 37. This upwardly directed peripheral wall 37 is designed so as to be interposed in the space 16 between the outer peripheral wall 15 of the upper lid X and the depending peripheral wall 17. Four receiving pillars 40 coinciding with the notches 38 of the lower lid Y are formed in the space 16 of this upper lid X so that the upper end of the upwardly directed peripheral wall 37 of the lower lid will not totally contact the lower surface c of the upper lid X with a space 41 defining a "labyrinth" for the smoke being maintained to allow smoke to enter the interior through this labyrinth 41. Further, the above mentioned partition pillars 39 prevent smoke coming along the outer periphery of the upwardly directed peripheral wall 37 and direct it to enter the labyrinth 41. Item 42 is a circular window hole made in the centre of the lower lid Y. The lower surface d of this lower lid Y is a sloped surface sloping upwardly toward the outer periphery from the circular window hole in the centre (see FIGS. 3 and 4). Item 43 is a window cover made of a metal and mounted on the upper surface of the lower lid Y, which is provided with a circular recessed part 44 formed to fit in the circular window hole 42 and with many small holes 45 made at regular intervals near the outer periphery in the recessed part 44. This recessed part 44 is positioned above the hole edge 42a of the circular window hole 42 so that smoke rising from the lower surface will accumulate in this spacing 46 and enter the detector through the small holes 45. Item 47 is an elastic sheet mounted on the window cover 43, and having a large hole 48 made in it. Item 49 is a circular holding plate made of a metal, which is mounted on the elastic sheet 47 and fixed with screws 50 to the lower lid Y along with the sheet 47 and window cover 43. Items 51 are small projections provided on the upper surface e of the lower lid Y into which the screws 50 screw. Item 52 is another small projection projected on the upper surface so as to determine the positions of the window cover 43, sheet 47 and holding plate 49. Hole 53 is a hole made in the above described three component parts 43, 47 and 49. Hole 54 is a hole made in the centre of the holding plate 49 so that smoke which has passed through the small holes 45 in the window cover 43 will come to the optical system part Z in the upper lid X through said hole 54 from the large hole 48 in the sheet 47. Item 55 is a U-shaped metal piece having both side pieces 55a fixed to the holding plate 49 across above the hole 54. Both side pieces 55a are provided with respective outward directed pieces 55b so as to be well-seated, and 55c is a lower piece connecting both side pieces 55a with each other. Item 56 is an elastic mat pasted to the holding plate 49 so as to seal the barrier 27 mounted to the upper lid X when the upper and lower lids X and Y are fastened together, with this mat 56 being made of, for example, sponge or rubber. Item 57 is a fastening screw to fasten the upper and lower lids X and Y (see FIGS. 3 and 4), which is inserted in the center of the upper lid X from its upper surface b and screwed in the lower piece 55c of the U-shaped metal piece 55 in the lower lid Y. The head of this screw 57 is aligned with the pulling-in port 4 in the base plate Xa so that the screw 57 may be operated with a screw driver through the pulling-in port 4. That is to say, the screw 57 can be removed through the pulling-in port 4, the upper and lower lids X and Y can be separated from each other and the interior through which an electric current being passed can be checked without removing the electric wires connected to the terminal plates 5 on the base plate Xa and with the base plate Xa and upper lid X electrically connected with each other as they are. Item 58 is a C-shaped ring for preventing the screw 57 from coming out, which is pressed into a hole 59 from the lower surface c of the upper lid X and engaged with the hole 59 by its own resiliency. By fastening this screw 57, the U-shaped metal piece 55 and the rivets 31 of the base plate 26 are electrically connected with each other.

In FIGS. 7 and 8 showing the present embodiment, all the parts shown as dotted are preferably black colored parts or made of a material having a proper color and properly surface-treated to prevent reflection so that the light from the light source 24 will be absorbed by the surfaces of these parts.

Figure 13:
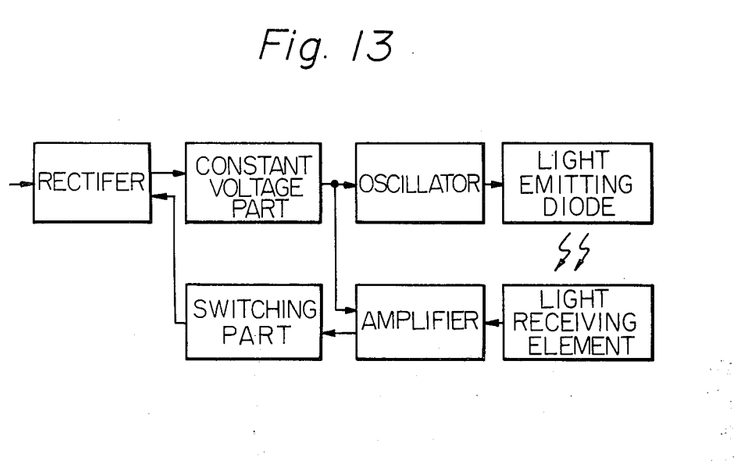
FIG. 13 is a block diagram showing an exemplary interior structure of the detector according to the present invention.

The operation of the light scattering type smoke detector of the present invention shall be explained. The light source 24 which comprises a light emitting diode emits intermittently a light with the current source from one chamber 13 including a constant voltage device and oscillator (see FIG. 13). This light is normally prevented by the barriers 27 and 28 from being projected on the light receiving element 25 so that the light receiving element receives no light and does not operate. In such case, the light of the light source 24 is thought to make a slight scrambling reflection (noise light) within the upper and lower lids X and Y and yet the detector does not switch and thus its operating state is not yet reached.

When smoke is generated by fire or the like, it will come in through the small holes 45 in the window cover 43 of the lower lid Y and through the labyrinth 41 between the upper and lower lids X and Y, and will flow into the upper and lower lids X and Y through the hole 54 in the holding plate 49.

Figure 14:
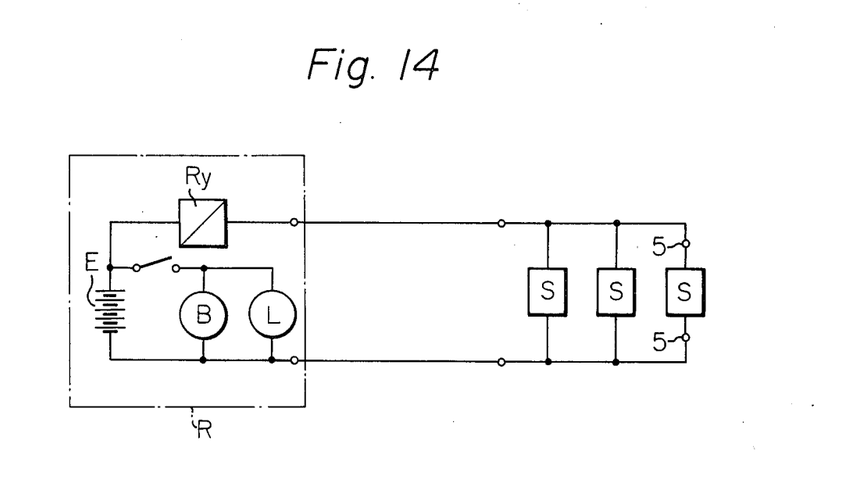
FIG. 14 is a circuitry diagram showing an exemplary arrangement of the detector and an associated warning device in the present invention.

When this smoke flows in, the light will be scattered by the particles of the smoke and will be projected on the light receiving element 25. Such scattered light irradiated onto the receiving element 25 is converted therein to an electrical signal, which is amplified by an amplifier. When the amplified signal reaches a certain level, a switching part in the next stage is actuated so that an impedance across the smoke detector S, that is, across the terminal plates 5 of the base plate Xa, is lowered to a value of several ohms, whereupon a relay Ry in a receiver R as shown in FIG. 14 is actuated so as to actuate or light such means as an alarm bell B, warning lamp L and the like, or either one of them, to provide an alarm signal.

Figure 12A:
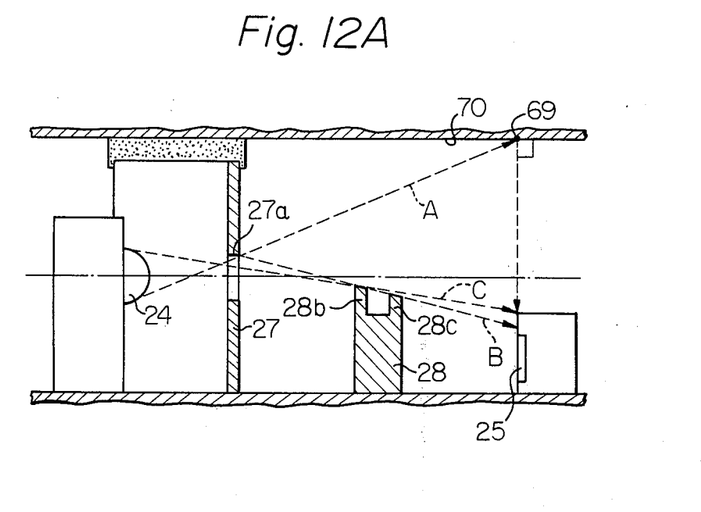
FIG. 12A and 12B are explanatory views of the operation of the optical system.
Figure 12B:
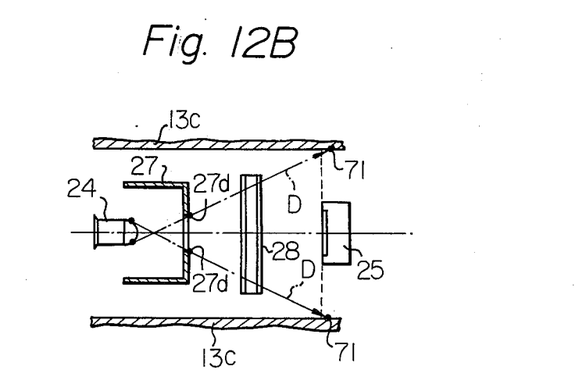

The relation of the light source, barriers and light receiving element shall now be detailed in the following. In FIGS. 12A and 12B showing the operation in the optical system or optical bench block respectively in its vertically sectioned and horizontally sectioned fragmental views, the intersection 69 of a straight line A passing through the light source 24 and the tip edge 27a of the first barrier 27 with the inside surface of the upper plate 70 is so set as to be farther behind the light source 24 than the light receiving element 25; a straight line B passing through the tip edge 27a of the barrier 27 and the tip edge 28c (the third barrier) of the barrier 28 is positioned above the light receiving element 25; a straight line C passing through the light source 24 and the tip edge 28b (the second barrier) of the barrier 28 is positioned above the tip edge 28c of the barrier and the light receiving element 25; and a straight line D passing through the tip edges 28b and 28c of the barrier 28 is so arranged as to be positioned above the light receiving element 25.

By arranging them as described above, usually the light of the light emitting source reflected at the tip edges of the first barrier 27a and second barrier 28b is interrupted by the third barrier 28c so as not to be projected on the light receiving element 25.

Further, the optical system is so arranged that intersections 71 of straight lines D connecting the light source 24 and both side edges 27d of the barrier 27 with chamber walls 13c of the chambers 13 will be behind the light receiving element 25 with respect to the light source 24, as seen in FIG. 12B.

Figure 4:
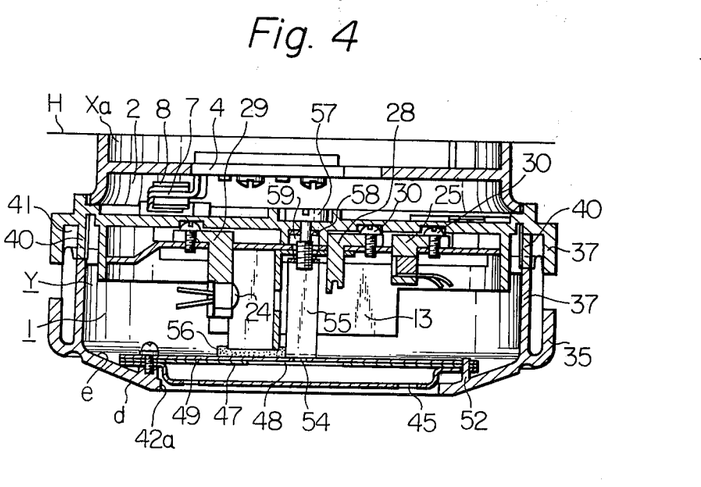
FIG. 4 is a sectioned view on line IV—IV in FIG. 1.

The mat 56 on the holding plate 49 also contributes to the desired arrangement for the optimum optical system since the mat 56 is adapted to cover the downward opening of the barrier 27 (see in this connection FIG. 4).

In the present invention, the base plate 26 to which the light source 24, light receiving element 25 and barriers 27 and 28 are fixed is arranged within the detector body 1 so as to be parallel with the fitting surface (for example, the ceiling surface H) for the detector body 1 so that, in case the diffused light of the light source 24 is refracted in the direction vertical to the fitting surface, the light receiving element 25 will detect it and operate in response to it. Accordingly, the direction (the vertical direction here) vertical to the fitting surface can be used for the light detecting direction. As a result, the space in the horizontal direction can be utilized for such other purposes as, for example, the arrangements of the current source part and amplifying part and thus the interior of the detector body 1 can be effectively utilized.

In the present invention, the upper and lower lids X and Y are connected with each other in the center with one screw 57 inserted from the upper lid X and are fitted to the ceiling H. The base plate Xa provided with the terminal plates 5 for the input and output is separated from the upper lid X so as to be electrically connected removably from the upper lid X. Further, the port 4 for pulling in the electric wires connected to the terminal plates 5 is made in the center of the base plate Xa, such that both the pulling-in port 4 and screw 57 for connecting the upper and lower lids X and Y are made to coincide with each other so that the screw 57 can be operated through the pulling-in port 4. Therefore, the screw 57 can be operated from the pulling-in port 4 in said base plate Xa without removing the base plate Xa connected with the electric wires and the upper lid X such that the lower lid Y can be removed without interrupting the current to allow the current passing through the internal component parts to be simply checked.

In the present invention, the detector body 1 is divided into the upper and lower lids X and Y, the fitting plate 26 for the optical system part Z is fitted in the center of the upper lid X, the surface opposed to the lower lid Y is opened at 13b on both sides of this base plate 26, the right and left chambers 13 each enclosed on the four sides are formed integrally with said upper lid X and such electric parts 18 and 19 as the oscillating part and amplifying part are shielded and contained in the right and left chambers 13 through their openings 13b. Therefore, the containing parts for the component parts 18 and 19 can be formed simultaneously with the molding of the upper lid X, with the results that thus printing plates and metal cases are unnecessary, the number of the component parts is reduced, the containing parts are formed on both sides of the optical system part Z of the upper lid Z to enable the space within the detector body 1 to be effectively utilized.

In the present invention, the detector body 1 is divided into the upper and lower lids X and Y, optionally one of these lids, for example, the upper lid X, is provided with the optical system part Z, current source part and amplifying part, whereas the other one of the lids which is here Y is provided with the metal plate 49 to shield electric noises. One screw 57 passing through the centre of the upper lid X to connect the upper and lower lids X and Y is screwed into the metal piece 55 on the metal plate 49 in the lower lid Y and is fastened to press the metal piece 55 against the metal plate 26 to which is connected with the return wire 21 for preventing noises of the upper lid X. This alignment enables the upper and lower lids X and Y to be connected and disconnected with each other by fastening and loosening the single screw 57, the electrical connection between the shielding metal plate 49 and the noise preventing return wire 21 with each other being completed simultaneously with the connection of the upper and lower lids X and Y such that the detector can be connected and disconnected without additional electrical connections and also without the lead wires contacting the metal plate 26 at the time of sweeping the dust.

In the present invention, the detector body 1 made of a symthetic resin to contain the light source 24 and light receiving element 25 is divided into the upper and lower lids X and Y, both the upper and lower lids X and Y have the integrally formed peripheral walls 15, 17, 35 and 37 projecting from one lid toward the other lid, the peripheral walls 15, 17, 35 and 37 of both lids X and Y are respectively combined with each other to form the labyrinth so that smoke will snake in along the peripheral walls 15, 17, 35 and 37 and the external light will be interrupted. Therefore, the detector is lower in its own height than conventional ones. A plurality of barriers or light shielding plates are piled up on the lower surface of the body and can be made simultaneously with the molding of the upper and lower lids X and Y, rendering the detector simple to manufacture.

In the present invention, further, the base plate Xa to be fitted to the ceiling H and provided with the terminal plates 5 for the input and output is separated from the detector body 1 provided with the light source 24 and light receiving element 25 and is formed to be circular. This base plate Xa and the body 1 are removably rotated and hung with the inserted blades 7 and receiving blades 8 and the inserted blades 7 or receiving blades 8 positioned on the upper surface b of the body 1 are fixed to the projecting parts 9 so as to be elevated above the upper surface b. The circular receiving step 11 for determining the rotary position of the circular base plate Xa is integrally formed on the upper surface b of the body 1 and cuts 12 for draining water are made in some places of the receiving step 11. Therefore, water drops deposited on the upper surface b of the body 1 are caused to flow out through the cuts 12 without accumulating and, further, the inserted blades 7 or receiving blades 8, which are electrical parts fixed to the upper surface b of the body 1, are elevated by the projecting parts 9 whereby any electrical troubles as a result of water accumulation can be more positively prevented. The rotary position of the circular base plate Xa is fixed by means of the circular receiving step 11 provided with the water draining cuts 12 and, therefore, the rotary hanging by means of the inserted blades 7 and receiving blades 8 is positive.

What is claimed is:
1. A light-scattering smoke detector comprising:
   a mounting base having a substantially planar upper surface and means to facilitate mounting said base to a room ceiling surface;
   an optical system comprising a horizontally disposed base plate, a light emitting element depending from one longitudinal end of said base plate, a light receiving element depending from the other longitudinal end of said base plate and a light shielding means consisting of a plurality of elements depending from said base plate and disposed between said light emitting element and said light receiving element;
   an upper lid member substantially of a vertically disposed cylindrical shape closed at its upper end, said upper lid being provided with means for coupling the same with said mounting base, said upper lid member having a pair of chambers depending therefrom at horizontally symmetrical positions with respect to a diametrical plane through said lid member, said pair of chambers being spaced from one another and formed integrally with said lid member, an electric source part housed in one of said chambers and electrically connected with the light emitting element, and an amplifying part housed in the other one of said chambers and electrically connected with the light receiving element, said base plate being mounted to said upper lid member between said pair of chambers with said light emitting element, said light receiving element, and said light shielding means oriented along said diametrical plane; and,
   a lower lid member substantially of a vertically disposed cylindrical shape, said lower lid member having a horizontally disposed lower surface with a plurality of smoke-admitting holes therein, said lower lid member being coupled to said upper lid member to form a substantially cylindrical chamber, the junction between said lid members defining a smoke lead-in path.

2. A smoke detector according to claim 1, each of said pair of chambers comprising vertically depending walls integrally formed with the upper lid.

3. A smoke detector according to claim 2, said light shielding means comprising a first, second and third shielding plate, each of said pair of chambers integrally formed with said upper lid member having a portion of said vertically depending walls parallel to and on opposite sides of said diametrical plane, the intersections with said parallel portions of said vertically depending walls of straight lines extending from the light emitting element through tip edges of the first shielding plate being positioned behind the light receiving element with respect to the light emitting element, a straight line passing respective tip edges of the first and third shielding plates being positioned inside the light receiving element with respect to the diametrical plane of said system, a straight line passing respective tip edges of the second and third shielding plates being positioned likewise inside the light receiving element, and a straight line extended from the light emitting element through the tip edge of the second shielding plate being positioned likewise inside the third shielding plate and light receiving element.

4. A smoke detector according to claim 1, said light emitting element being disposed in a chamber defined by one of said light shielding means, said element having a U-shaped section with two side openings, one of said side openings being adjacent said base plate, the other of said side openings being adjacent said lower surface of said lower lid member.

5. A smoke detector according to claim 1, said means for coupling said lid member with said mounting base comprising at least two electrically conductive terminal blades attached to one of said members and electrically conductive receiving elements for said terminal blades attached to the other of said members, said elements attached to said mounting base being connected to a source of electricity such that when said terminal blades are inserted into said receiving elements, said lower lid is both mechanically coupled to said mounting base and electrically coupled to said source of electricity.

6. A smoke detector according to claim 1 wherein said lower lid is provided with a metal plate for shielding electrical noise, said metal plate having a U-shaped mounting member extending upward therefrom, said upper and lower lids being coupled together by a screw passing through said upper lid into said mounting member which presses said mounting member against a metal plate in said upper lid which is electrically connected to a return line for preventing noise.

7. A smoke detector according to claim 1 wherein each of said upper and lower lids are provided with a peripheral wall formed integrally and projecting in the direction toward the other lid, said peripheral walls of the respective lids being adapted to form a labyrinth clearance between them when both lids are assembled together such that any smoke is caused to enter into the detector body through said labyrinth clearance while external light is shielded from entering said cylindrical chamber within said upper and lower lids.

* * * * *